(12) United States Patent
Sato et al.

(10) Patent No.: US 12,004,880 B2
(45) Date of Patent: Jun. 11, 2024

(54) RISK MANAGEMENT DEVICE, RISK MANAGEMENT METHOD, AND NON-TEMPORARY RECORDING MEDIUM IN WHICH RISK MANAGEMENT PROGRAM IS STORED

(71) Applicant: Omron Healthcare Co., Ltd., Kyoto (JP)

(72) Inventors: Hironori Sato, Kyoto (JP); Sirui Yeap, Kyoto (JP); Fumihiko Nakamura, Kyoto (JP); Daisuke Nozaki, Kyoto (JP)

(73) Assignee: OMRON HEALTHCARE CO., LTD., Kyoto (JP)

( * ) Notice: Subject to any disclaimer, the term of this patent is extended or adjusted under 35 U.S.C. 154(b) by 605 days.

(21) Appl. No.: 17/097,571

(22) Filed: Nov. 13, 2020

(65) Prior Publication Data
US 2021/0059613 A1    Mar. 4, 2021

Related U.S. Application Data

(63) Continuation of application No. PCT/JP2019/020043, filed on May 21, 2019.

(30) Foreign Application Priority Data

May 22, 2018    (JP) ................................ 2018-097906

(51) Int. Cl.
*A61B 5/00* (2006.01)
*A61B 5/0205* (2006.01)
(Continued)

(52) U.S. Cl.
CPC .......... *A61B 5/7275* (2013.01); *A61B 5/0205* (2013.01); *G16H 10/60* (2018.01);
(Continued)

(58) Field of Classification Search
CPC .... A61B 5/7275; A61B 5/0205; G16H 10/60; G16H 50/30
See application file for complete search history.

(56) References Cited

U.S. PATENT DOCUMENTS

2011/0201902 A1    8/2011    Shiga et al.
2015/0265170 A1    9/2015    Wisløff et al.
(Continued)

FOREIGN PATENT DOCUMENTS

CN    102216951 A    10/2011
JP    2002-157339 A    5/2002
(Continued)

OTHER PUBLICATIONS

English translation of the International Preliminary Report on Patentability, dated Nov. 26, 2020, for International Application No. PCT/JP2019/020043.
(Continued)

*Primary Examiner* — Tammie K Marlen
(74) *Attorney, Agent, or Firm* — Birch, Stewart, Kolasch & Birch, LLP

(57) ABSTRACT

A risk management device includes an acquisition unit configured to acquire biological information relating to a biological parameter of an evaluation subject and behavior information relating to a behavior parameter of the evaluation subject, a risk calculation unit configured to calculate an event occurrence rate, based on the biological information being acquired and the behavior information being acquired, a selection unit configured to select a biological parameter and a behavior parameter that serve as an improvable factor from the biological information and the behavior information, a contribution calculation unit configured to calculate a contribution to the event occurrence rate for each of the biological parameter and the behavior parameter selected as the improvable factor, and a generation unit configured to
(Continued)

generate output data indicating a calculation result in the contribution calculation unit.

7 Claims, 11 Drawing Sheets

(51) Int. Cl.
  *G16H 10/60* (2018.01)
  *G16H 50/30* (2018.01)
  *A61B 5/021* (2006.01)
  *A61B 5/145* (2006.01)

(52) U.S. Cl.
  CPC .............. *G16H 50/30* (2018.01); *A61B 5/021* (2013.01); *A61B 5/14546* (2013.01)

(56) References Cited

U.S. PATENT DOCUMENTS

| | | |
|---|---|---|
| 2017/0061093 A1 | 3/2017 | Amarasingham et al. |
| 2017/0357771 A1* | 12/2017 | Connolly ............... G16H 50/30 |
| 2018/0247713 A1* | 8/2018 | Rothman ........... A61B 5/02055 |
| 2019/0008466 A1* | 1/2019 | Shimota ................. G06V 40/20 |

FOREIGN PATENT DOCUMENTS

| | | |
|---|---|---|
| JP | 2010-122901 A | 6/2010 |
| JP | 5812333 B2 | 4/2013 |
| JP | 2017-508589 A | 3/2017 |
| WO | 2010058698 A1 | 5/2010 |

OTHER PUBLICATIONS

Ito, "Exercise Therapy for Primary Prevention of Coronary Heart Disease," Nippon Rinsho, vol. 69, Suppl. 7, Sep. 20, 2011, pp. 491-494 (7 pages total).

Taniguchi et al., "Diet and Cancer," Journal of Clinical and Experimental Medicine, vol. 202, No. 12, Sep. 21, 2002, pp. 967-971.

Written Opinion of the International Searching Authority for International Application No. PCT/JP2019/020043, dated Aug. 27, 2019, with an English translation.

Chinese Office Action and Search Report dated Oct. 24, 2023 for corresponding Application No. 201980027559.4 with an English translation.

Chinese Office Action for corresponding Chinese Application No. 201980027559.4, dated Mar. 20, 2024, with English translation.

Uchiyama, "Correct treatment and life maintenance for stroke," Guanguchi Scientific and Technical Press, Jul. 1, 2010, pp. 23-25 (4 pages total).

* cited by examiner

[FIG. 1]
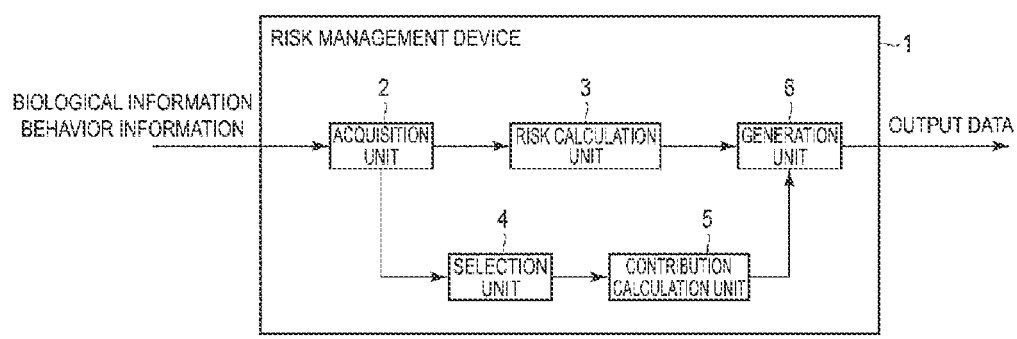
[FIG. 2]
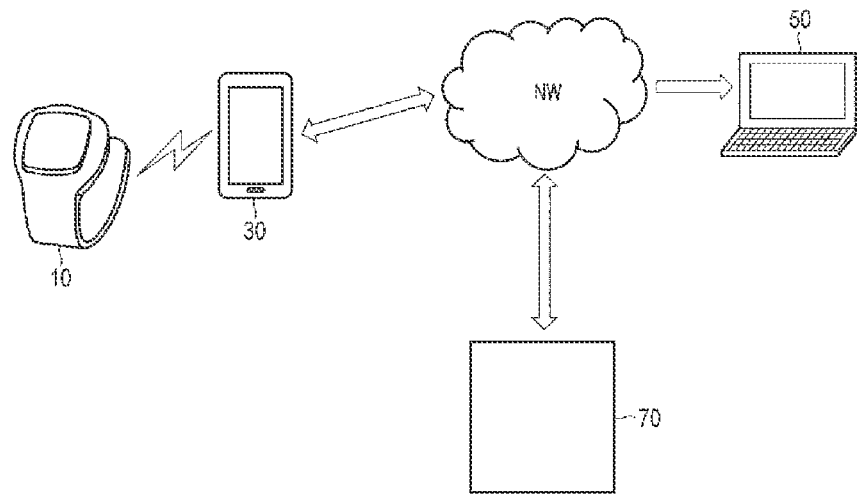

[FIG. 3]
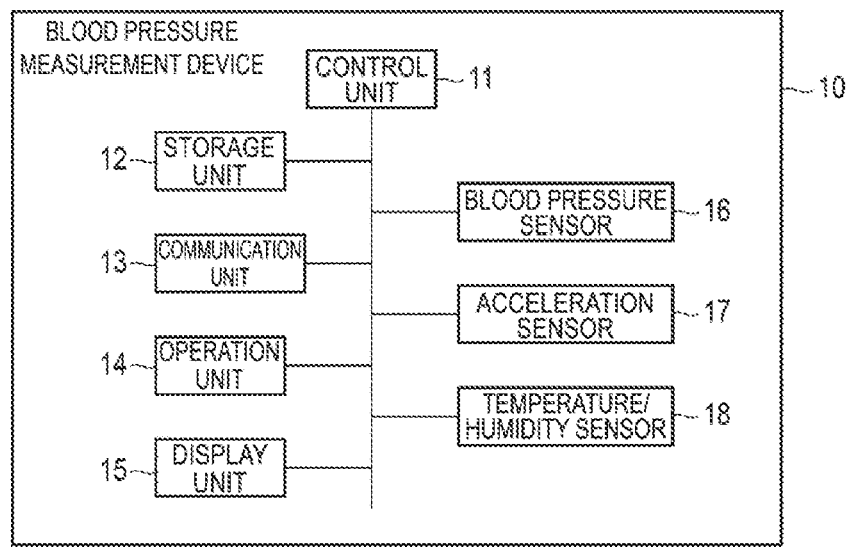
[FIG. 4]
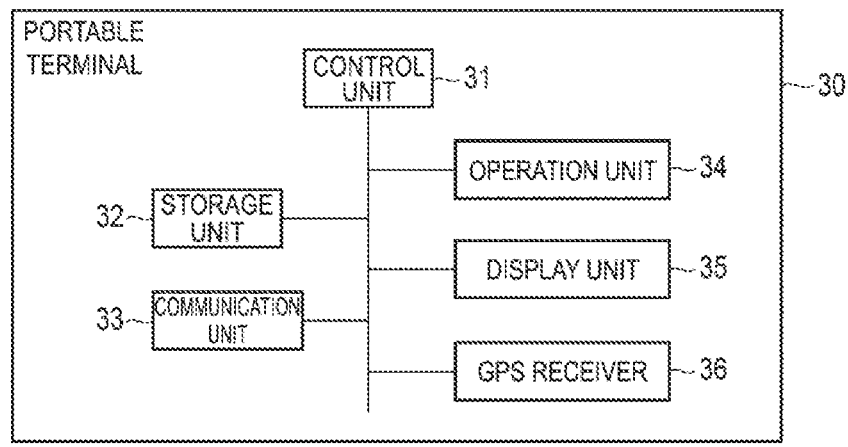

[FIG. 5]
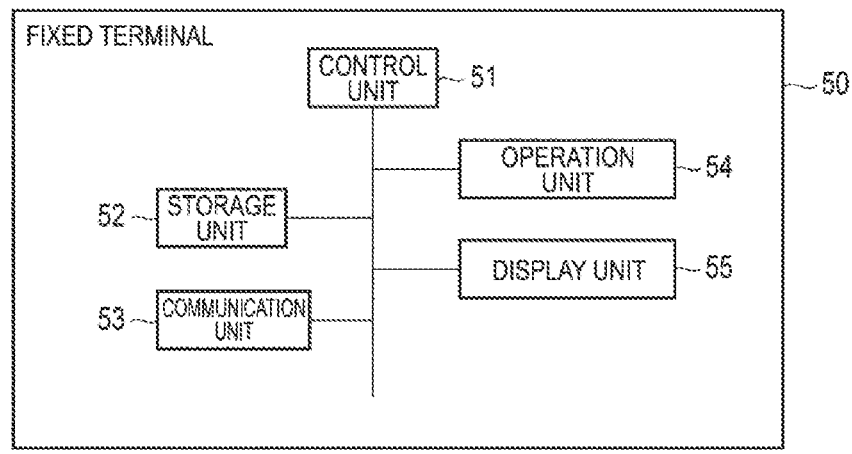
[FIG. 6]
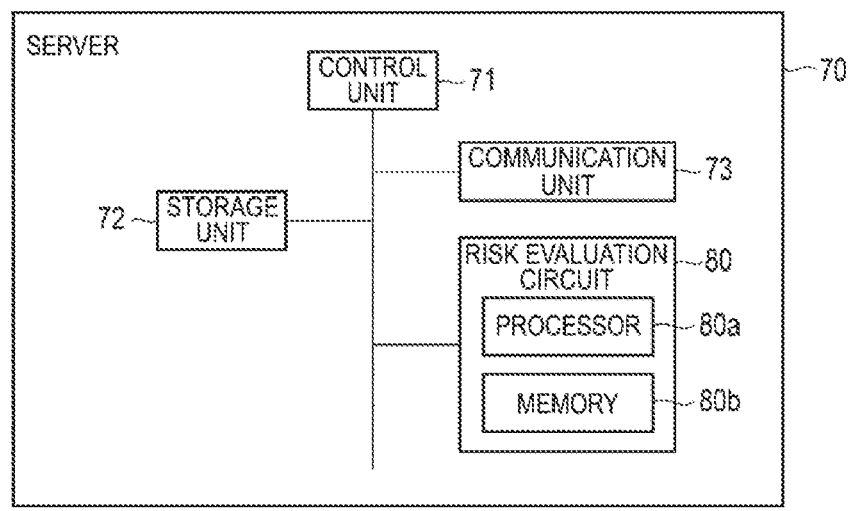

[FIG. 7]
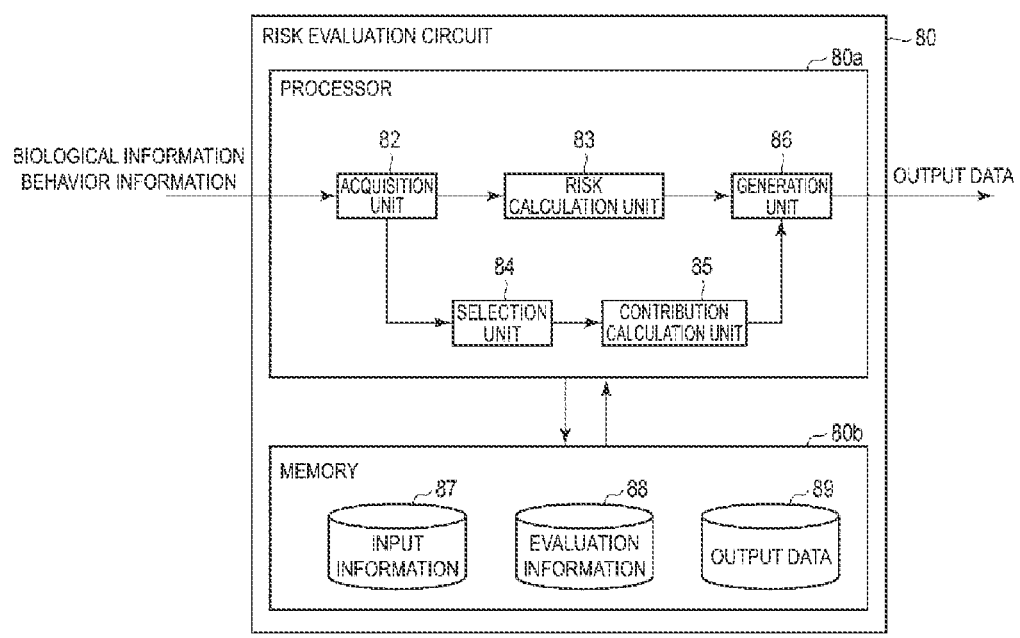

[FIG. 8]
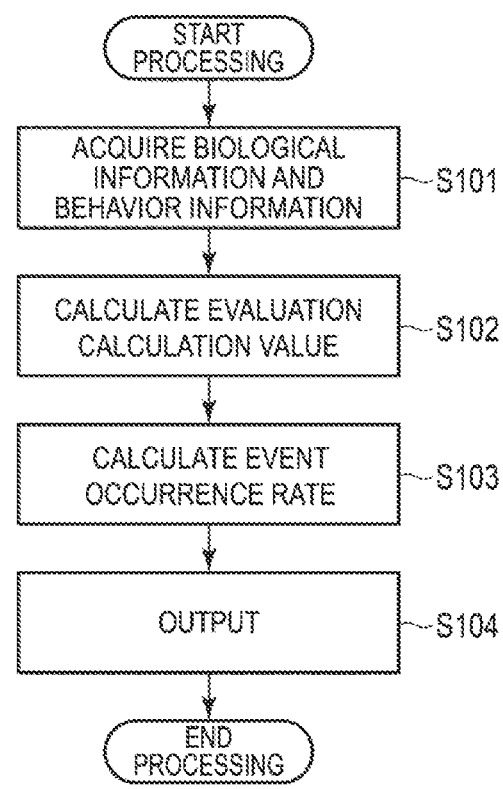

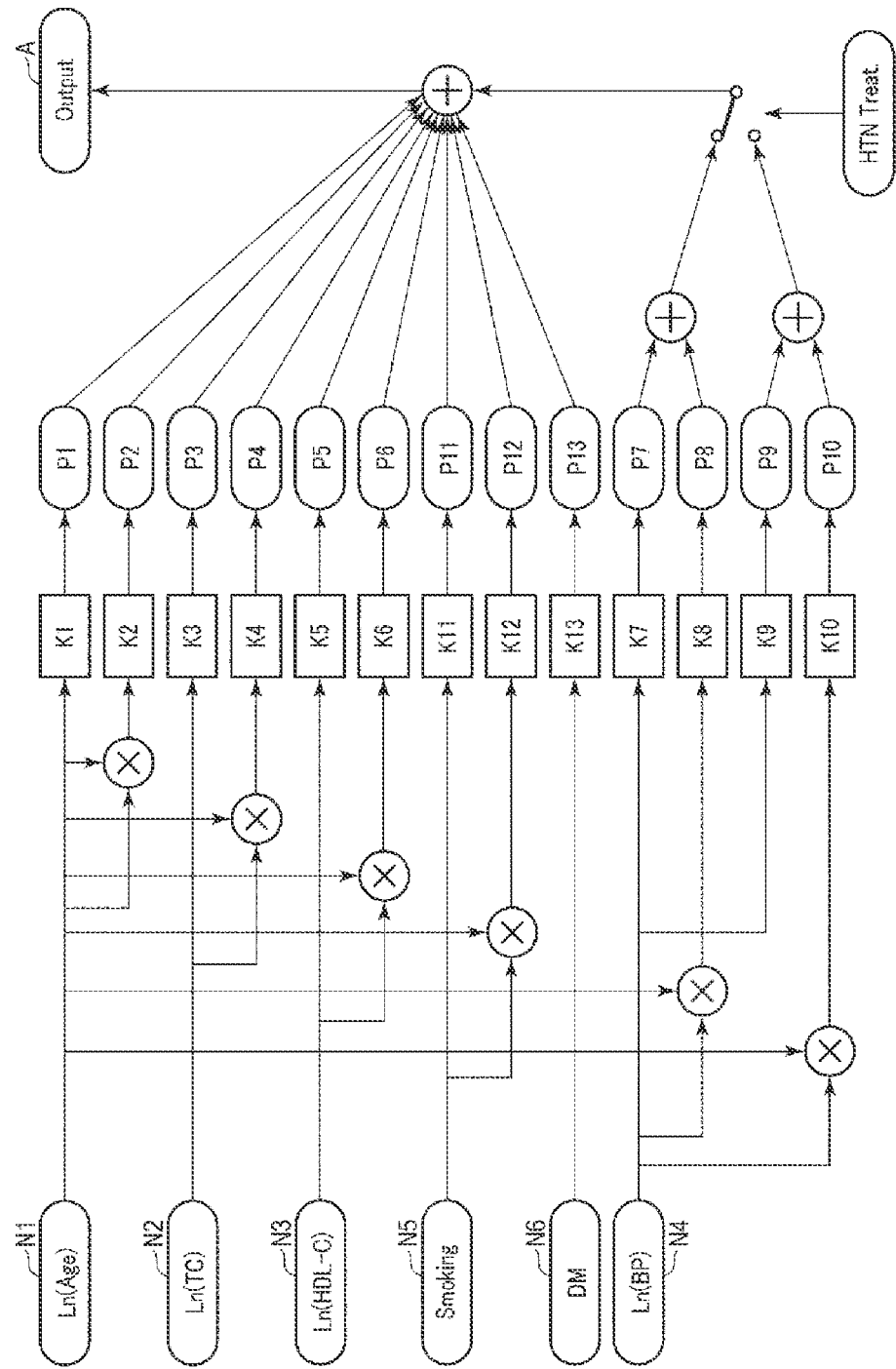
[FIG. 9]

[FIG. 10]

|  | Women | | Men | |
| --- | --- | --- | --- | --- |
|  | White | AA | White | AA |
| K1 | -29.799 | 17.114 | 12.344 | 2.469 |
| K2 | 4.884 | 0 | 0 | 0 |
| K3 | 13.54 | 0.94 | 11.853 | 0.302 |
| K4 | -3.114 | 0 | -2.664 | 0 |
| K5 | -13.578 | -18.92 | -7.99 | -0.307 |
| K6 | 3.149 | 4.475 | 1.769 | 0 |
| K7 | 2.019 | 29.291 | 1.797 | 1.916 |
| K8 | 0 | -6.432 | 0 | 0 |
| K9 | 1.957 | 27.82 | 1.764 | 1.809 |
| K10 | 0 | -6.087 | 0 | 0 |
| K11 | 7.574 | 0.691 | 7.837 | 0.549 |
| K12 | -1.665 | 0 | -1.795 | 0 |
| K13 | 0.661 | 0.874 | 0.658 | 0.645 |
|  |  |  |  |  |
| M | -29.18 | 86.61 | 61.18 | 19.54 |
| BS | 0.9655 | 0.9533 | 0.9144 | 0.8954 |

[FIG. 11]
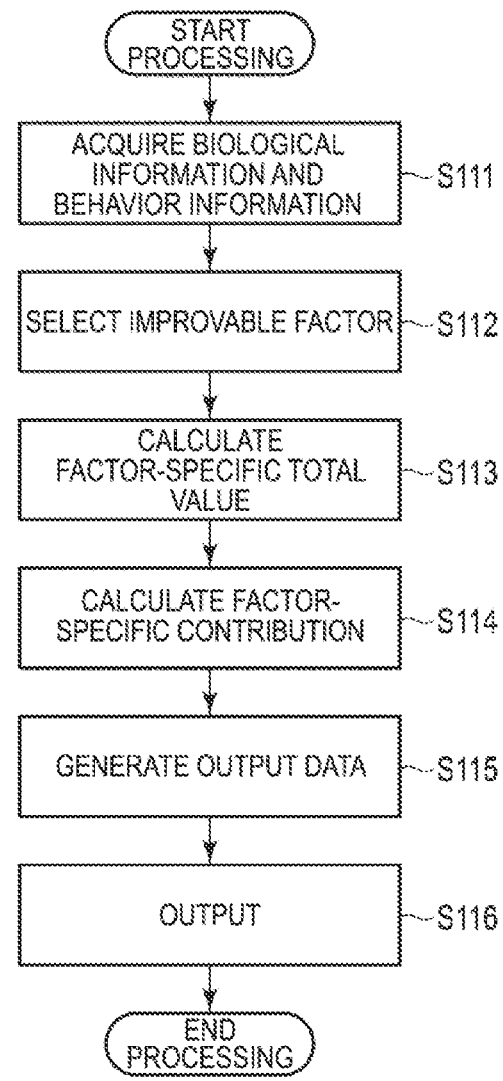

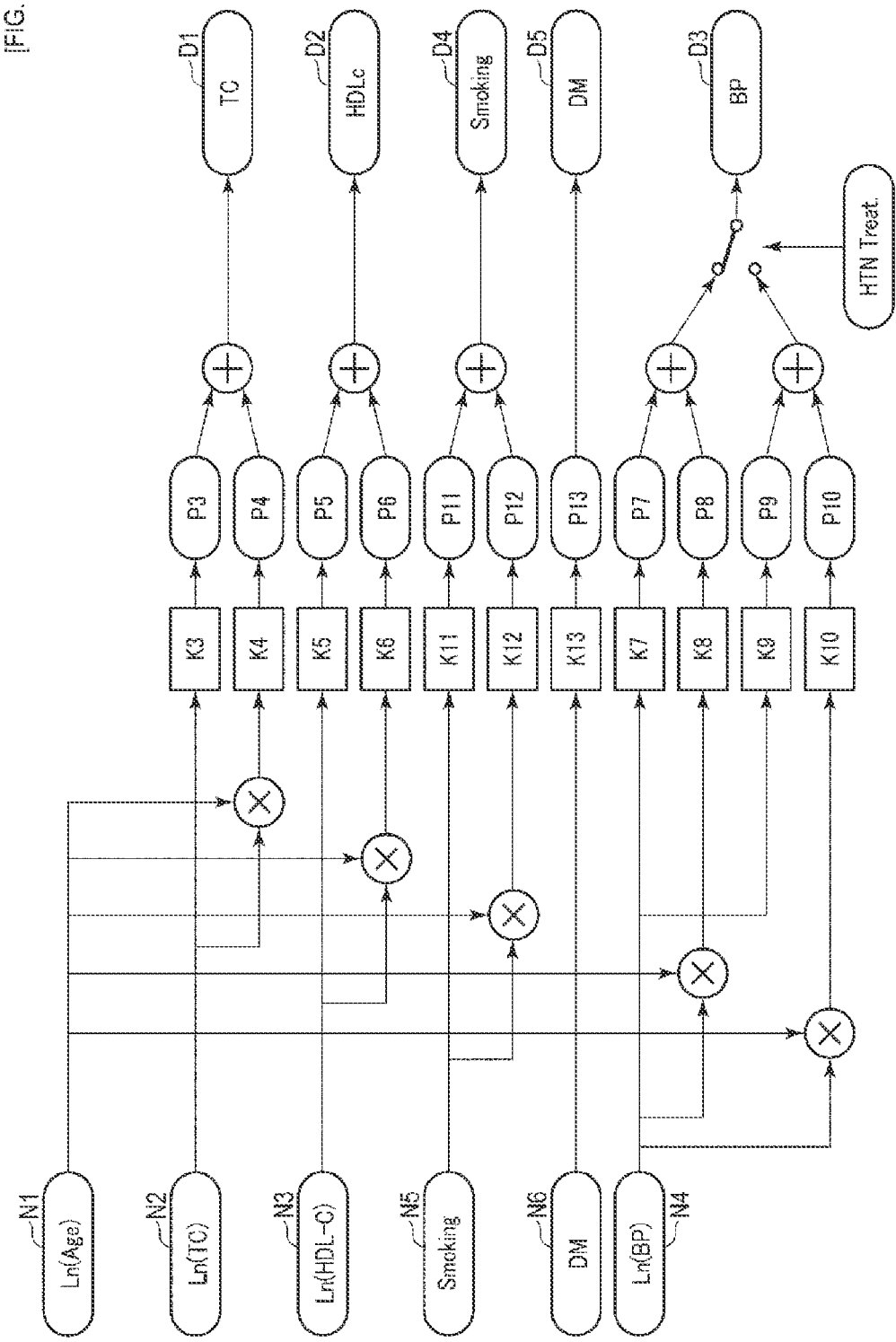
[FIG. 12]

[FIG. 13]
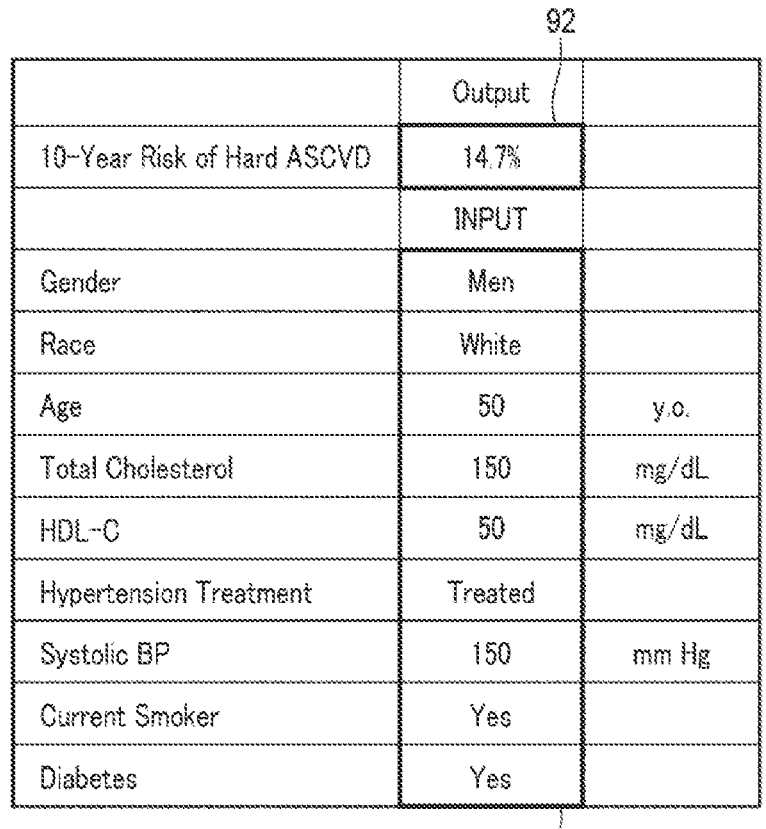
[FIG. 14]
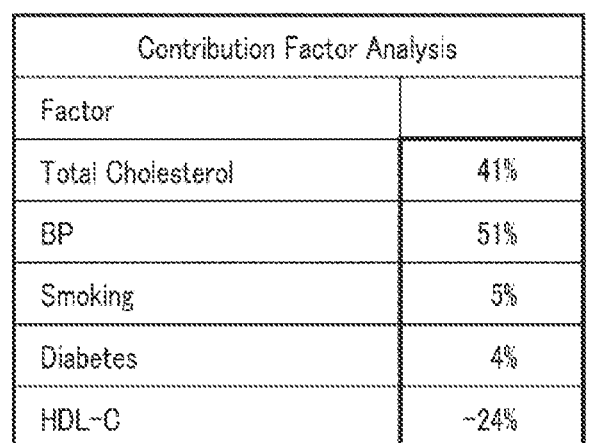

[FIG. 15]
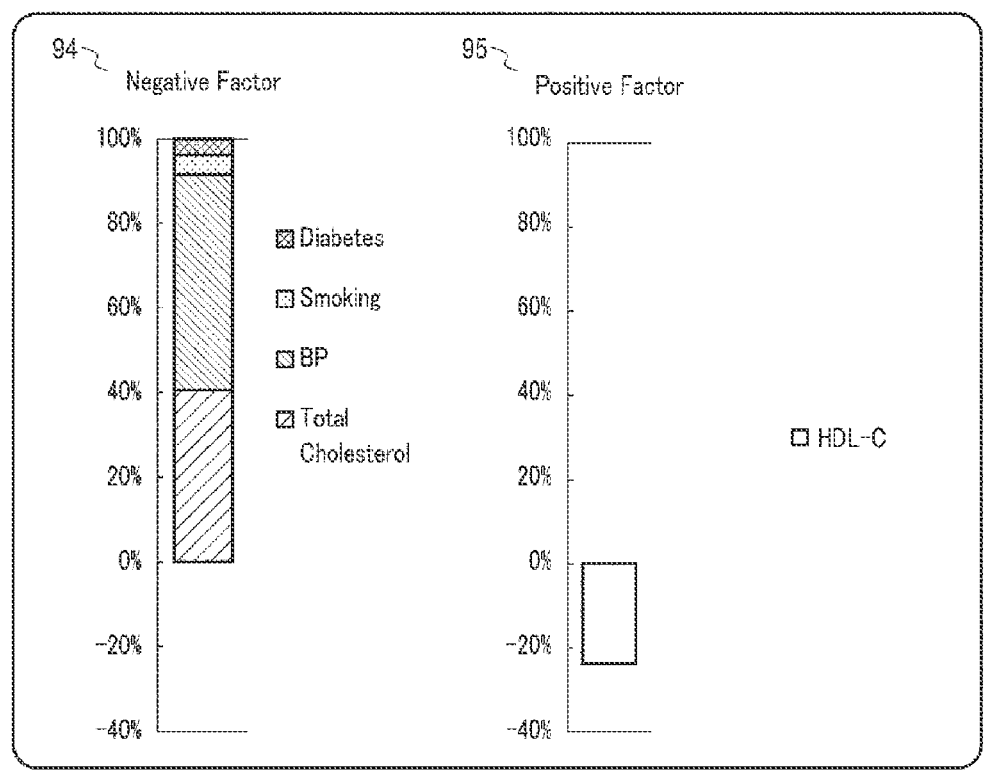

RISK MANAGEMENT DEVICE, RISK MANAGEMENT METHOD, AND NON-TEMPORARY RECORDING MEDIUM IN WHICH RISK MANAGEMENT PROGRAM IS STORED

CROSS-REFERENCE TO RELATED APPLICATIONS

This application is the U.S. national stage application filed pursuant to 35 U.S.C. 365(c) and 120 as a continuation of International Patent Application No. PCT/JP2019/020043, filed May 21, 2019, which application claims priority from Japanese Patent Application No. 2018-097906, filed May 22, 2018, which applications are incorporated herein by reference in their entireties.

TECHNICAL FIELD

The invention relates to a risk management device, a risk management method, and a non-temporary recording medium in which a risk management program is stored, capable of calculating an event occurrence rate relating to an evaluation subject.

BACKGROUND ART

Patent Document 1 discloses a life-and-death prediction device. The life-and-death prediction device calculates a mortality rate within 10 years of a subject by using input information such as gender, a total cholesterol level, and presence or absence of diabetes.

CITATION LIST

Patent Literature

Patent Document 1: JP 5812333 B

SUMMARY OF INVENTION

Technical Problem

In the life-and-death prediction device in Patent Document 1, the mortality rate within 10 years is displayed, but it is difficult to determine which measurement result pushes up the mortality rate within 10 years. Thus, it is difficult to determine which cause leads to an increase in risk, and it is difficult to determine what kind of action needs to be taken to reduce the risk.

The present invention has been made in view of the above-described circumstances, and an object of the present invention is to provide a risk management device, a risk management method, and a non-temporary recording medium in which a risk management program is stored, capable of easily recognizing a cause that greatly contributes to an increase in risk.

Solution to Problem

The present invention takes the following measures in order to solve the problem described above.

In other words, a risk management device according to an example of the present disclosure includes an acquisition unit configured to acquire biological information relating to a biological parameter of an evaluation subject and behavior information relating to a behavior parameter of the evaluation subject, a risk calculation unit configured to calculate an event occurrence rate, based on the biological information being acquired and the behavior information being acquired, a selection unit configured to select a biological parameter and a behavior parameter that serve as an improvable factor from the biological information and the behavior information, a contribution calculation unit configured to calculate a contribution to the event occurrence rate for each of the biological parameter and the behavior parameter selected as the improvable factor, and a generation unit configured to generate output data indicating a calculation result in the contribution calculation unit.

According to the configuration described above, a cause that pushes up an event occurrence rate can be easily recognized by comparing contributions to the event occurrence rate by factor. In this way, it is clear which biological parameter or behavior parameter pushes up the event occurrence risk, and it is easy to determine how to reduce the risk.

Further, in the configuration described above, a parameter that can be improved by the evaluation subject is selected as an improvable factor from the parameter of each piece of the acquired biological information and the acquired behavior information. Then, a factor-specific contribution to the event occurrence rate is presented for the selected improvable parameter. Thus, according to the configuration described above, a user can recognize a cause that is improvable and greatly contributes to a reduction in an event occurrence risk, and can easily determine how to reduce the risk. Further, the contribution may be calculated for only the parameter selected as the improvable factor, and thus a calculation amount can be reduced further than that when the contribution is calculated for all factors. In this way, a processing load and a memory capacity of the device can be suppressed.

In the risk management device according to the example described above, the risk calculation unit calculates an occurrence risk of arteriosclerotic cardiovascular disease as the event occurrence rate.

In the risk management device according to the example described above, the acquisition unit acquires, as the biological information, at least one of race, gender, age, a blood pressure value, a cholesterol level, presence or absence of diabetes, and genetic information.

In the risk management device according to the example described above, the acquisition unit acquires at least one of a smoking status and sleep time as the behavior information.

In the risk management device according to the example described above, the selection unit selects, as the improvable factor, at least one of a blood pressure value, a cholesterol level, presence or absence of diabetes, presence or absence of smoking, and sleep time.

In the risk management device according to the example described above, the generation unit generates, as the output data, image data configured to compare the contributions of the biological parameter and the behavior parameter selected as the improvable factor with each other.

In the risk management device according to the example described above, the contribution calculation unit calculates an evaluation value for the event occurrence rate for each of the biological parameter and the behavior parameter selected as the improvable factor, calculates an additional value acquired by totaling the calculated evaluation values, and calculates, as the contribution, a proportion of each of the evaluation value of the biological parameter and the evaluation value of the behavior parameter to the calculated additional value.

In the risk management device according to the example described above, the improvable factor includes a negative factor that contributes to an increase in the event occurrence rate and a positive factor that contributes to a reduction in the event occurrence rate, and the contribution calculation unit calculates, as the additional value, a total value of the evaluation value calculated for each of the biological parameter and the behavior parameter selected as the negative factor of the improvable factor.

Advantageous Effects of Invention

The present invention can provide a risk management device, a risk management method, and a non-temporary recording medium in which a risk management program is stored, capable of easily recognizing a cause that greatly contributes to an increase in risk.

BRIEF DESCRIPTION OF DRAWINGS

FIG. 1 is a block diagram illustrating a functional configuration of a risk management device according to an application example.

FIG. 2 is a schematic diagram illustrating a configuration of a risk evaluation system including the risk management device according to a first embodiment.

FIG. 3 is a block diagram illustrating a hardware configuration of a blood pressure measurement device according to the first embodiment.

FIG. 4 is a block diagram illustrating a hardware configuration of a portable terminal according to the first embodiment.

FIG. 5 is a block diagram illustrating a hardware configuration of a fixed terminal according to the first embodiment.

FIG. 6 is a block diagram illustrating a hardware configuration of a server according to the first embodiment.

FIG. 7 is a block diagram illustrating a functional configuration of a risk evaluation circuit as an example of the risk management device according to the first embodiment.

FIG. 8 is a flowchart illustrating a procedure of risk calculation processing in the risk evaluation circuit as an example of the risk management device according to the first embodiment.

FIG. 9 is a schematic diagram illustrating processing performed in the risk calculation processing in the risk evaluation circuit as an example of the risk management device according to the first embodiment.

FIG. 10 is a diagram illustrating a table used in the risk calculation processing in the risk evaluation circuit as an example of the risk management device according to the first embodiment.

FIG. 11 is a flowchart illustrating a procedure of contribution calculation processing in the risk evaluation circuit as an example of the risk management device according to the first embodiment.

FIG. 12 is a schematic diagram illustrating processing performed in the contribution calculation processing in the risk evaluation circuit as an example of the risk management device according to the first embodiment.

FIG. 13 is a diagram illustrating a display screen used in the risk calculation processing in the risk evaluation circuit as an example of the risk management device according to the first embodiment.

FIG. 14 is a diagram illustrating a display screen illustrating a contribution by factor in the contribution calculation processing in the risk evaluation circuit as an example of the risk management device according to the first embodiment.

FIG. 15 is a diagram illustrating a display screen illustrating a contribution by factor imaged in the contribution calculation processing in the risk evaluation circuit as an example of the risk management device according to the first embodiment.

DESCRIPTION OF EMBODIMENTS

Now, with reference to the drawings, embodiments are described. Note that, in the following description, components having the same function and configuration are denoted with a shared reference symbol. Further, when a plurality of components having a shared reference symbol are distinguished from one another, a distinction is made by adding additional symbols following the shared reference symbol. Note that, when there is no particular need in distinguishing a plurality of components, the plurality of components are denoted only with a shared reference symbol without an additional symbol.

1. Application Example

First, an example of a risk management device to which the present invention is applied is described by using FIG. 1.

As illustrated in FIG. 1, a risk management device 1 includes an acquisition unit 2, a risk calculation unit 3, a selection unit 4, a contribution calculation unit 5, and a generation unit 6. The risk management device 1 performs risk calculation processing and contribution calculation processing, based on a risk evaluation program. The risk evaluation program is an example of a risk management program.

The acquisition unit 2 acquires input information relating to an evaluation subject. The input information includes biological information and behavior information.

The biological information is information relating to a biological parameter of the evaluation subject. The biological information includes one or more factors. The biological information includes, as a factor, gender, race, age, a total cholesterol level, an HDL cholesterol level, an LDL cholesterol level, presence or absence of hypertension treatment, a blood pressure value, presence or absence of diabetes, genetic information, and the like, for example.

The behavior information is information relating to a behavior parameter of the evaluation subject. The behavior information includes one or more factors. The behavior information includes, as a factor, a smoking status, sleep time, and the like, for example.

The risk calculation unit 3 calculates an event occurrence rate of the evaluation subject, based on the input information. The event occurrence rate is, for example, an ASCVD occurrence risk within 10 years (10-year risk of hard ASCVD event), an ASCVD occurrence risk in a lifetime, and the like. For example, the ASCVD occurrence risk within 10 years is acquired by predicting a possibility that an arteriosclerotic cardiovascular disease (ASCVD) such as a heart attack and an ischemic stroke occurs within 10 years, and converting the possibility into numbers.

The selection unit 4 extracts input information relating to an improvable factor from the input information. The improvable factor is a factor due to a cause that can be improved by the evaluation subject. The improvable factor is, for example, a total cholesterol level, an HDL cholesterol level, an LDL cholesterol level, a blood pressure value, presence or absence of smoking, presence or absence of diabetes, sleep time, and the like.

The contribution calculation unit 5 calculates a contribution to the event occurrence rate for each improvable factor, based on the input information relating to the improvable factor extracted by the selection unit 4. The contribution to the event occurrence rate is a contribution of the improvable factor to the event occurrence rate.

The generation unit 6 generates output data, based on a calculation result of the event occurrence rate and a calculation result of the contribution by factor. The output data is, for example, data for presenting a calculation result of the event occurrence rate. Further, the output data is, for example, image data for comparably presenting a contribution of each improvable factor. The generation unit 6 outputs the generated output data to the outside.

In the configuration as described above, a user can easily recognize a cause that pushes up an event occurrence rate by comparing contributions to the event occurrence rate by factor. In other words, according to the configuration described above, it is clear which measurement result pushes up a risk, and thus it is easy for the user to determine how to reduce the risk.

Further, according to the configuration described above, even when an evaluation of input information about all factors falls within a normal range, the user can recognize a cause that greatly contributes to an increase in risk by comparing contributions to an event occurrence rate by factor.

Further, in the configuration described above, an item that can be improved by an evaluation subject among acquired input information is extracted as an improvable factor. Then, a factor-specific contribution to an event occurrence rate is presented for the improvable item. Thus, for example, the evaluation subject can easily recognize a cause that is improvable and has a great influence on a reduction in risk, and can easily determine how to reduce the risk.

2. First Embodiment

A first embodiment of the risk management device according to the application example described above is described below. A risk evaluation system that includes a portable terminal including a risk evaluation circuit as an example of the risk management device is described below.

2.1 Overall Configuration Example

FIG. 2 is a diagram schematically illustrating an example of an application scene of the risk evaluation system according to the present embodiment. The risk evaluation system according to the present embodiment is a system for calculating an ASCVD occurrence risk within 10 years by using biological information and behavior information of an evaluation subject, and storing or presenting a calculation result of the ASCVD occurrence risk within 10 years.

As illustrated in FIG. 2, the risk evaluation system includes a blood pressure measurement device 10 and a portable terminal 30. The blood pressure measurement device 10 and the portable terminal 30 are connected by near-field wireless communication or wired communication. The risk evaluation system may further include a fixed terminal 50 and a server 70. In this case, the portable terminal 30 is connected to each of the fixed terminal 50 and the server 70 via a network NW. In this way, the blood pressure measurement device 10 can be connected to each of the fixed terminal 50 and the server 70 via the portable terminal 30. In other words, the blood pressure measurement device 10 can communicate with each of the fixed terminal 50 and the server 70 via the portable terminal 30. In the present embodiment, for example, communication between the portable terminal 30, the fixed terminal 50, and the server 70 may adopt communication via the network NW, but the present invention is not limited thereto, and near-field wireless communication or wired communication may be adopted. The portable terminal 30 and the fixed terminal 50 are an example of a terminal device.

The blood pressure measurement device 10 is a wearable device to be worn at a freely-selected measurement portion (for example, a wrist). The blood pressure measurement device 10 measures a blood pressure value of the evaluation subject at the measurement portion. The blood pressure measurement device 10 can transmit blood pressure information including a measurement result of a blood pressure value and the like to the portable terminal 30. Further, the blood pressure measurement device 10 can transmit activity information including sleep information and the like to the portable terminal 30.

For example, the portable terminal 30 is a terminal that can be carried by the evaluation subject. The portable terminal 30 receives the blood pressure information and the activity information from the blood pressure measurement device 10. The portable terminal 30 transfers the received blood pressure information and the received activity information to the fixed terminal 50 and the server 70. Further, the portable terminal 30 receives biological information and behavior information about the evaluation subject from the server 70.

For example, the fixed terminal 50 is a terminal that can be operated by a physician, the evaluation subject, and the like. The fixed terminal 50 receives blood pressure information from the portable terminal 30. The fixed terminal 50 generates diagnostic information relating to the evaluation subject, based on the received blood pressure information and the biological information relating to the evaluation subject. The fixed terminal 50 transmits the generated diagnostic information to the portable terminal 30 and the server 70.

The server 70 is a server computer that accumulates information transmitted from the portable terminal 30, the fixed terminal 50, and the like.

The server 70 includes a risk evaluation circuit 80. The risk evaluation circuit 80 calculates, for example, an ASCVD occurrence risk within 10 years for the evaluation subject, based on the biological information and the behavior information. The biological information includes the blood pressure information received from the blood pressure measurement device 10, the diagnostic information stored in a storage unit 72, and the like. The behavior information includes the sleep information received from the blood pressure measurement device 10, and the like. The biological information and the behavior information are stored in an electronic medical chart or the like. Further, the risk evaluation circuit 80 selects an improvable factor from among factors included in the biological information and the behavior information. Then, the risk evaluation circuit 80 calculates a contribution to the ASCVD occurrence risk within 10 years for the improvable factor. The risk evaluation circuit 80 generates output data, based on a calculation result of the ASCVD occurrence risk within 10 years and a calculation result of the contribution. The portable terminal 30 displays the output data generated by the risk evaluation circuit 80, the diagnostic information received from the fixed terminal 50, and the like.

2.2 Hardware Configuration Examples

An example of a hardware configuration of each of the devices in the risk evaluation system according to the present embodiment is described.

2.2.1 Hardware Configuration Example of Blood Pressure Measurement Device

First, a hardware configuration example of the blood pressure measurement device 10 according to the present embodiment is described. FIG. 3 is a block diagram illustrating an example of the hardware configuration of the blood pressure measurement device 10 according to the present embodiment. As illustrated in FIG. 3, the blood pressure measurement device 10 according to the present embodiment includes a control unit 11, a storage unit 12, a communication unit 13, an operation unit 14, a display unit 15, and a blood pressure sensor 16. The blood pressure measurement device 10 may further include at least one of an acceleration sensor 17 and a temperature/humidity sensor 18.

The control unit 11 includes a central processing unit (CPU), a random access memory (RAM), a read only memory (ROM), and the like, and controls each component according to information processing. Further, the control unit 11 includes a clock (not illustrated), and has a function of acquiring current date and time. The control unit 11 may have a function of displaying the acquired date and time on the display unit 15.

The control unit 11 generates blood pressure information, activity information, and environment information, based on measurement results by the blood pressure sensor 16, the acceleration sensor 17, and the temperature/humidity sensor 18. The blood pressure information includes, for example, a measurement result of a blood pressure value of an evaluation subject by the blood pressure sensor 16, and the like. The activity information includes an activity amount, the number of steps, and a sleep condition of the evaluation subject based on a measurement by the acceleration sensor 17. The environment information includes temperature and humidity in the periphery of the evaluation subject based on a measurement by the temperature/humidity sensor 18. Each piece of the blood pressure information, the activity information, and the environment information is associated with measurement date and time based on current date and time acquired by the clock. Further, each piece of the blood pressure information, the activity information, and the environment information may further be associated with a device ID for uniquely identifying the blood pressure measurement device 10.

The storage unit 12 is, for example, an auxiliary storage device such as a solid state drive. When the blood pressure measurement device 10 is configured as a large device to some extent instead of a small device such as a clock type, the storage unit 12 may be a hard disk drive. The storage unit 12 stores a program executed by the control unit 11, the blood pressure information, the activity information, the environment information, and the like.

The communication unit 13 is a communication interface for performing communication with the portable terminal 30. For example, the communication unit 13 transmits the blood pressure information, the activity information, the environment information, and the like to the portable terminal 30. In the present embodiment, for example, communication with the portable terminal 30 by the communication unit 13 may adopt near-field wireless communication, such as Bluetooth (trade name), but the present invention is not limited thereto. For example, communication performed by the communication unit 13 may adopt communication via the network NW such as a local area network (LAN) or wired communication through use of a communication cable.

For example, the operation unit 14 includes a user interface such as a touch panel and an operation button. The operation unit 14 detects an operation performed by the evaluation subject through the user interface, and outputs a signal indicating a content of the operation to the control unit 11.

The display unit 15 includes, for example, a display screen (for example, a Liquid Crystal Display (LCD), an Electroluminescence (EL) display, or the like), an indicator, and the like. The display unit 15 displays information in accordance with a signal from the control unit 11, and notifies the evaluation subject of the information. For example, the display unit 15 can display the blood pressure information, the activity information, the environment information, and the like stored in the storage unit 12.

The blood pressure sensor 16 measures a blood pressure value of the evaluation subject. The blood pressure value includes a representative index such as systolic blood pressure and diastolic blood pressure, for example. Although the following description describes, as an example, that the blood pressure value is the systolic blood pressure, the diastolic blood pressure and another index may be used instead of the systolic blood pressure, and the plurality of indexes may be used in combination.

The blood pressure sensor 16 may be, for example, a continuous measurement type that can measure blood pressure of the evaluation subject per beat (continuously) of a heart rate, or a non-continuous measurement type that can measure blood pressure at a spot (non-continuously) for a predetermined time. For example, the continuous measurement type blood pressure sensor 16 may adopt a method of measuring blood pressure of the evaluation subject continuously based on pulse transit time (PTT), a method (tonometry method) of measuring blood pressure continuously based on a pressure pulse wave, and the like. Note that the method of measuring blood pressure continuously is not limited to the above-mentioned examples, and a method of detecting a pulse wave through use of a light emitting element and the like may be adopted as appropriate. For example, the non-continuous measurement type blood pressure sensor 16 may adopt a method of detecting a pulse wave by applying a pressure on a blood vessel through use of a cuff as a pressure sensor (oscillometric method).

The acceleration sensor 17 detects, as a group of three-axial components, acceleration of a portion of the evaluation subject wearing the blood pressure measurement device 10. Further, the acceleration sensor 17 may further include a gyro sensor, and may further detect an angular velocity as a group of three-axial components in addition to acceleration.

The temperature/humidity sensor 18 measures temperature and humidity in the periphery of the evaluation subject.

2.2.2 Hardware Configuration Example of Portable Terminal

Next, a hardware configuration example of the portable terminal 30 is described. FIG. 4 is a block diagram illustrating an example of the hardware configuration of the portable terminal 30 according to the present embodiment. As illustrated in FIG. 4, the portable terminal 30 according to the present embodiment includes a control unit 31, a storage unit 32, a communication unit 33, an operation unit 34, a display unit 35, and a global positioning system (GPS) receiver 36.

The control unit 31 and the storage unit 32 are similar to the control unit 11 and the storage unit 12 of the blood pressure measurement device 10, respectively. The storage unit 32 of the portable terminal 30 stores information received from the blood pressure measurement device 10 and position information generated by the GPS receiver 36. The information received from the blood pressure measurement device 10 includes blood pressure information, activity information, environment information, and the like.

The communication unit 33 is a communication interface for performing communication with the blood pressure measurement device 10, the fixed terminal 50, and the server 70. For example, the communication unit 33 receives the blood pressure information, the activity information, the environment information, and the like from the blood pressure measurement device 10. Further, the communication unit 33 transmits the blood pressure information, the activity information, the environment information, the position information, and the like to the fixed terminal 50 and the server 70.

The operation unit 34 and the display unit 35 are similar to the operation unit 14 and the display unit 15 of the blood pressure measurement device 10, respectively.

The GPS receiver 36 measures a position of the portable terminal 30, and generates the position information. For example, the position information includes a positioning date/time and a latitude and a longitude of the portable terminal 30 at the positioning date/time. For example, positioning performed by the GPS receiver 36 may be performed in synchronization with measurement performed by the blood pressure sensor 16 of the blood pressure measurement device 10.

2.2.3 Hardware Configuration Example of Fixed Terminal

Next, a hardware configuration example of the fixed terminal 50 is described. FIG. 5 is a block diagram illustrating an example of the hardware configuration of the fixed terminal 50 according to the present embodiment. As illustrated in FIG. 5, the fixed terminal 50 according to the present embodiment includes a control unit 51, a storage unit 52, a communication unit 53, an operation unit 54, and a display unit 55.

The control unit 51 and the storage unit 52 are similar to the control unit 11 and the storage unit 12 of the blood pressure measurement device 10, respectively. The control unit 51 of the fixed terminal 50 generates biological information relating to the evaluation subject, diagnostic information relating to the evaluation subject, and the like.

The storage unit 52 of the fixed terminal 50 temporarily stores information transferred from the portable terminal 30, the biological information relating to the evaluation subject, the diagnostic information relating to the evaluation subject, and the like.

The communication unit 53 is a communication interface for performing communication with the portable terminal 30 and the server 70. For example, the communication unit 53 receives the blood pressure information, the activity information, the environment information, and the like from the portable terminal 30. Furthermore, the communication unit 53 transmits the biological information relating to the evaluation subject, the diagnostic information relating to the evaluation subject, and the like to the portable terminal 30 and the server 70.

The operation unit 54 and the display unit 55 are similar to the operation unit 14 and the display unit 15 of the blood pressure measurement device 10, respectively. In the operation unit 54, the biological information acquired by various types of inspection devices can be input. The biological information may be recorded to the server 70 via a network such as an in-hospital LAN.

2.2.4 Hardware Configuration Example of Server

Next, a hardware configuration example of the server 70 is described. FIG. 6 is a block diagram illustrating an example of the hardware configuration of the server 70 according to the present embodiment. As illustrated in FIG. 6, the server 70 according to the present embodiment includes a control unit 71, the storage unit 72, a communication unit 73, and the risk evaluation circuit 80.

The risk evaluation circuit 80 is an example of the risk management device. In the present embodiment, the risk management device is provided in the server 70, but may be provided in any of the blood pressure measurement device 10, the portable terminal 30, and the fixed terminal 50.

The control unit 71 and the storage unit 72 are similar to the control unit 11 and the storage unit 12 of the blood pressure measurement device 10, respectively. The storage unit 72 of the server 70 stores information and the like transmitted from the portable terminal 30 and the fixed terminal 50.

The communication unit 73 is a communication interface for performing communication with the portable terminal 30 and the fixed terminal 50. For example, the communication unit 73 receives the blood pressure information, the activity information, the environment information, and the like from the portable terminal 30. For example, the communication unit 73 receives the blood pressure information, the activity information, the environment information, and the like from the fixed terminal 50. Further, the communication unit 73 receives the biological information relating to the evaluation subject, the diagnostic information relating to the evaluation subject, and the like from the fixed terminal 50. The communication unit 73 transmits the information stored in the storage unit 72 to the portable terminal 30 and the fixed terminal 50.

The risk evaluation circuit 80 includes, for example, a processor 80*a* and a memory 80*b*. The risk evaluation circuit 80 achieves various operational control, data processing, and the like by executing a program stored in the memory 80*b* by the processor 80*a*. Further, the risk evaluation circuit 80 includes a clock (not illustrated), and can measure current date and time.

The processor 80*a* is a CPU or a micro processing unit (MPU) including, for example, an arithmetic circuit, and the like. The processor 80*a* can perform control of each unit and data processing by executing a program stored in the memory 80*b* or the storage unit 32.

The memory 80*b* includes, for example, a non-volatile memory that stores a program executed by the processor 80*a* and a volatile memory such as a RAM used as a working memory.

The risk evaluation circuit 80 executes risk calculation processing and contribution calculation processing, based on a risk evaluation program. The risk evaluation program is an example of the risk management program. The risk calculation processing and the contribution calculation processing by the risk evaluation circuit 80 are described later. The risk evaluation program is a program for causing the risk calculation processing and the contribution calculation processing to be executed by the risk evaluation circuit 80. The risk evaluation program may be stored in the memory 80*b* or stored in the storage unit 32.

Note that the control unit 71 may function as the risk evaluation circuit 80. In other words, the control unit 71 may also serve as the risk evaluation circuit 80. In this case, the CPU of the control unit 71 serves as the processor 80*a* of the risk evaluation circuit 80, the ROM of the control unit 71 serves as the non-volatile memory of the memory 80*b* of the risk evaluation circuit 80, and the RAM of the control unit 71 serves as the volatile memory of the memory 80*b* of the risk evaluation circuit 80.

2.3 Functional Configuration Example

Next, an example of a functional configuration of the risk evaluation system according to the present embodiment is described.

2.3.1 Functional Configuration Example of Risk Evaluation Circuit

FIG. 7 is a block diagram schematically illustrating an example of a functional configuration of the risk evaluation circuit 80 of the risk evaluation system according to the present embodiment.

The processor 80*a* of the risk evaluation circuit 80 develops the risk evaluation program stored in the non-volatile memory of the memory 80*b* in the volatile memory of the memory 80*b*. Then, the processor 80*a* functions as an acquisition unit 82, a risk calculation unit 83, a selection unit 84, a contribution calculation unit 85, and a generation unit 86 by interpreting and executing the risk evaluation program developed in the volatile memory.

The volatile memory of the memory 80*b* functions as an input information storage unit 87, an evaluation information storage unit 88, and an output data storage unit 89.

The input information storage unit 87 temporarily stores input information relating to the evaluation subject. The input information includes biological information and behavior information.

The biological information is information relating to a biological parameter of the evaluation subject. The biological information includes one or more factors. The biological information includes, as a factor, gender, race, age, a total cholesterol level, an HDL cholesterol level, presence or absence of hypertension treatment, a blood pressure value, and presence or absence of diabetes. The blood pressure value is a value of systolic blood pressure. The biological information may further include, as a factor, an LDL cholesterol level, genetic information, and the like.

The behavior information is information relating to behavior of the evaluation subject. The behavior information includes one or more factors. The behavior information includes a smoking status as a factor. The behavior information may further include sleep time as a factor.

The evaluation information storage unit 88 temporarily stores evaluation information relating to the evaluation subject. The evaluation information includes an ASCVD occurrence risk R within 10 years, a factor-specific contribution to the ASCVD occurrence risk within 10 years, and the like. The ASCVD occurrence risk R within 10 years is an example of an event occurrence rate. Further, the factor-specific contribution to the ASCVD occurrence risk within 10 years is an example of a contribution to the event occurrence rate.

The output data storage unit 89 temporarily stores output data for screen display.

The acquisition unit 82 acquires input information relating to the evaluation subject. The acquisition unit 82 acquires the input information from the storage unit 32, for example. The acquisition unit 82 stores the acquired input information in the input information storage unit 87 of the memory 80*b*, and also transmits the acquired input information to the risk calculation unit 83, the selection unit 84, and the contribution calculation unit 85.

The risk calculation unit 83 calculates the ASCVD occurrence risk R within 10 years, based on the input information. The risk calculation unit 83 stores a calculation result of the ASCVD occurrence risk R within 10 years in the evaluation information storage unit 88 of the memory 80*b*, and also transmits the calculation result to the generation unit 86.

The ASCVD occurrence risk within 10 years is acquired by predicting a possibility that an arteriosclerotic cardiovascular disease (ASCVD) such as a heart attack and an ischemic stroke occurs within 10 years, and converting the possibility into numbers. The ASCVD occurrence risk within 10 year is calculated based on, for example, a cardiovascular risk guideline (2013 ACC/AHA Guideline on the Assessment of Cardiovascular Risk) by ACC/AHA. The risk calculation processing by the risk calculation unit 83 is described later.

The selection unit 84 extracts input information relating to an improvable factor from the input information. The selection unit 84 stores the input information relating to the improvable factor in the evaluation information storage unit 88 of the memory 80*b*, and also transmits the input information to the contribution calculation unit 85.

The improvable factor is a factor caused by a cause that can be improved by the evaluation subject. The selection unit 84 selects, as the improvable factor, a total cholesterol level, an HDL cholesterol level, a blood pressure value, presence or absence of smoking, and presence or absence of diabetes. When the input information includes sleep time, the selection unit 84 may further select the sleep time as the improvable factor.

Further, the improvable factor can be classified into any of a positive factor and a negative factor. The positive factor is a factor that contributes to a reduction in the ASCVD occurrence risk R within 10 years. For example, an HDL cholesterol level is the positive factor. The negative factor is a factor that contributes to an increase in the ASCVD occurrence risk R within 10 years. For example, a total cholesterol level, a blood pressure value, a smoking status, and presence or absence of diabetes are the negative factors.

The contribution calculation unit 85 calculates a factor-specific contribution to the ASCVD occurrence risk R within 10 years for each improvable factor, based on the input information relating to the improvable factor. The factor-specific contribution is a contribution degree (contribution) of an improvable factor to the ASCVD occurrence risk R within 10 years.

The contribution calculation unit 85 stores the factor-specific contribution in the evaluation information storage unit 88 of the memory 80*b*, and also transmits the factor-specific contribution to the generation unit 86. The contribution calculation processing by the contribution calculation unit 85 is described later.

The generation unit 86 generates output data, based on a calculation result of the ASCVD occurrence risk R within 10 years and a calculation result of the factor-specific contribution. The output data is, for example, image data to be displayed on the display unit 35 of the portable terminal 30. The output data includes, for example, a calculation result of the ASCVD occurrence risk R within 10 years, a graph that can compare factor-specific contributions of improvable factors, and the like. Further, the generation unit 86 outputs the generated output data to the outside.

2.4 Operation Example

Next, an operation example of the risk evaluation system according to the present embodiment is described. Note that a processing procedure described below is merely an example, and each process may be changed to the extent possible. Further, in the processing procedure described below, steps can be omitted, substituted, and added in accordance with the embodiment as appropriate.

2.4.1 Operation Example of Risk Evaluation Circuit in Risk Calculation Processing FIG. 8 is a flowchart illustrating an example of a procedure of the risk calculation processing in the processor 80a of the risk evaluation circuit 80 according to the present embodiment. The processor 80a starts the risk calculation processing, based on, for example, an operation input for starting the risk calculation processing being performed on the operation unit 34 of the portable terminal 30.

In the risk calculation processing, the processor 80a first acquires, as input information, biological information and behavior information relating to an evaluation subject (S101). For example, the processor 80a acquires biological information and behavior information input by the operation unit 34 from the storage unit 32, and stores the biological information and the behavior information in the input information storage unit 87 of the memory 80b.

Next, the processor 80a calculates an evaluation calculation value A, based on the biological information and the behavior information stored in the input information storage unit 87 (S102). The evaluation calculation value A changes in accordance with the biological information and the behavior information for the evaluation subject.

FIG. 9 is a diagram schematically illustrating an example of a calculation procedure of the evaluation calculation value A (output). In the calculation of the evaluation calculation value A, the processor 80a first calculates integrated values P1 to P13, based on variables N1 to N6 and coefficients K1 to K13. Then, the processor 80a calculates the evaluation calculation value A by calculating a sum total of the integrated values P1 to P13. Note that, at this time, one of the integrated values P7 to P8 and the integrated values P9 to P10 is not used in the calculation of the evaluation calculation value A.

In FIG. 9, the variables N1 to N6 are variables relating to input information. The variable N1 is a natural logarithm of age of the evaluation subject. The variable N2 is a natural logarithm of a total cholesterol level of the evaluation subject. The variable N3 is a natural logarithm of an HDL cholesterol level of the evaluation subject. The variable N4 is a natural logarithm of a blood pressure value of systolic blood pressure of the evaluation subject. The variable N5 is a value indicating a smoking status of the evaluation subject. For example, the variable N5 is "1" when the evaluation subject is a smoker, and is "0" when the evaluation subject is not a smoker. The variable N6 is a value indicating presence or absence of diabetes of the evaluation subject. For example, the variable N6 is "1" when the evaluation subject is diabetic, and is "0" when the evaluation subject is not diabetic. Instead of the variable N5, a variable indicating sleep time may be used.

In FIG. 9, the coefficients K1 to K13 are constants used in the calculation processing of the ASCVD occurrence risk R within 10 years. Each of the coefficients K1 to K13 has a different value used according to race and gender of the evaluation subject. The value of each of the coefficients K1 to K13 is stored in the input information storage unit 87, for example. FIG. 10 is a table illustrating an example of values of the coefficients K1 to K13. In the example in FIG. 10, each of the coefficients K1 to K13 has a different value set according to gender (Men or Women) of the evaluation subject and race (White or AA) of the evaluation subject. In the example in FIG. 10, gender of the evaluation subject is classified into Men and Women, and race of the evaluation subject is classified into White and African American. The processor 80a sets a value corresponding to race, gender, and the like of a calculation subject for each of the coefficients K1 to K13, based on the input information stored in the input information storage unit 87 and the table in FIG. 10.

In FIG. 9, each of the integrated values P1 to P13 is calculated by using the variables N1 to N6 and the coefficients K1 to K13. For example, the integrated value P1 is a product of the variable N1 and the coefficient K1. Further, for example, the integrated value P2 is a product of a value acquired by squaring the variable N1 and the coefficient K2. Further, for example, the integrated value P4 is a product of the variable N2, the variable N1, and the coefficient K4.

Note that, in the calculation of the evaluation calculation value A, only one of the integrated values P7 and P8 and the integrated values P9 and P10 is used in the calculation of the evaluation calculation value A. Therefore, only one of the integrated values P7 and P8 and the integrated values P9 and P10 is reflected in the evaluation calculation value A. When input information indicating that treatment is being received for presence or absence of hypertension treatment is acquired, only the integrated values P7 and P8 are used in the calculation of the evaluation calculation value A. Further, when input information indicating that treatment is not yet received for presence or absence of hypertension treatment is acquired, only the integrated values P9 and P10 are used in the calculation of the evaluation calculation value A.

Next, the processor 80a calculates an ASCVD occurrence risk R within 10 years (10-Year Risk of Hard ASCVD Event), based on the biological information and the evaluation calculation value A (S103).

Formula (1) below is an example of a calculation formula used in the calculation of the ASCVD occurrence risk R within 10 years. In Formula (1), the ASCVD occurrence risk R within 10 years is calculated based on the evaluation calculation value A, a survival rate BS, and a reference value M.

[Equation 1]

$$R = 1 - BS^{\exp(A-M)} \qquad (1)$$

The survival rate BS is a survival rate (Baseline Survival) within 10 years relating to a subject with specific race and gender. The reference value M is a mean value (Mean) of the evaluation calculation value A in the entire subjects with specific race and gender. The survival rate BS and the reference value M are constants, and have different values used according to race and gender of an evaluation subject. An example of values of the survival rate BS and the reference value M is illustrated in FIG. 10. In the example in FIG. 10, the survival rate BS and the reference value M are set to different values according to gender (Men or Women) of the evaluation subject and race (White or AA) of the evaluation subject. The processor 80a sets a value corresponding to race, gender, and the like of a calculation subject for each of the survival rate BS and the reference value M, based on the input information and the table in FIG. 10.

Note that each of the coefficients K1 to K13, the survival rate BS, and the reference value M may have a different value set according to genetic information and the like of the evaluation subject.

Next, the processor 80a outputs the ASCVD occurrence risk R within 10 years calculated in S103 to the outside (S104). The processor 80a outputs the ASCVD occurrence risk R within 10 years to the control unit 31 of the portable terminal 30, for example. The ASCVD risk R within 10 years is displayed on, for example, the display unit 35 by the control unit 31.

2.4.2 Operation Example of Risk Evaluation Circuit in Contribution Calculation Processing FIG. 11 is a flowchart illustrating an example of a procedure of the contribution calculation processing in the processor 80a of the risk evaluation circuit 80 according to the present embodiment. The processor 80a starts the contribution calculation processing, based on, for example, an operation input for starting the contribution calculation processing being performed on the operation unit 34 of the portable terminal 30. Note that the contribution calculation processing may be performed simultaneously with the risk calculation processing described above, based on the operation input for starting the risk calculation processing.

In the contribution calculation processing, the processor 80a first acquires, as input information, biological information and behavior information relating to a specific evaluation subject (S111). For example, the processor 80a acquires biological information and behavior information input by the operation unit 34 from the storage unit 32.

Next, the processor 80a extracts an improvable factor from among a plurality of factors included in the input information (S112).

Next, the processor 80a calculates a factor-specific evaluation value for each improvable factor (S113). The factor-specific evaluation value contributes to the ASCVD occurrence risk R within 10 years. When other conditions are identical, the ASCVD occurrence risk R within 10 years increases with a greater factor-specific evaluation value. FIG. 12 is a diagram schematically illustrating an example of a calculation procedure of the factor-specific evaluation value.

In the calculation of the factor-specific evaluation value, the processor 80a first acquires integrated values P3 to P13, based on variables N1 to N6 and coefficients K3 to K13. For example, the processor 80a calculates the integrated values P3 to P13, based on the variables N1 to N6 and the coefficients K3 to K13. Each of the variables N1 to N6 and the coefficients K3 to K13 is calculated and set similarly to the risk calculation processing described above. Further, each of the integrated values P3 to P13 is calculated similarly to the risk calculation processing described above. Note that the integrated values P3 to P13 may be acquired by reading the integrated values P3 to P13 stored in the memory 80b in the risk calculation processing described above.

The factor-specific evaluation value includes a factor-specific evaluation value D1 for a total cholesterol level, a factor-specific evaluation value D2 for an HDL cholesterol level, a factor-specific evaluation value D3 for a blood pressure value, a factor-specific evaluation value D4 for a smoking status, and a factor-specific evaluation value D5 for diabetes. The factor-specific evaluation value D1 is a sum total of the integrated values P3 to P4. The factor-specific evaluation value D2 is a sum total of the integrated values P5 to P6. The factor-specific evaluation value D3 is a sum total of the integrated values P7 and P8, or the integrated values P9 and P10. The factor-specific evaluation value D4 is a sum total of the integrated values P11 to P12. Then, the integrated value P13 is used for the factor-specific evaluation value D5. The factor-specific evaluation values D1 and D3 to D5 are a positive value. The factor-specific evaluation value D2 is a negative value.

Note that only one of the integrated values P7 and P8 and the integrated values P9 and P10 is reflected in the factor-specific estimation value D3. For example, when input information indicating that treatment is being received for presence or absence of hypertension treatment is acquired, the integrated values P7 and P8 are reflected in the factor-specific evaluation value D3. Further, when input information indicating that treatment is not yet received for presence or absence of hypertension treatment is acquired, the integrated values P9 and P10 are reflected in the factor-specific evaluation value D3.

Next, the processor 80a calculates a factor-specific contribution to the ASCVD occurrence risk R within 10 years for each improvable factor, based on the factor-specific evaluation value (S114).

The factor-specific contribution is calculated as a proportion of the factor-specific evaluation value to an additional value acquired by totaling factor-specific evaluation values for improvable factors. The factor-specific contribution includes a factor-specific contribution C1 for a total cholesterol level, a factor-specific contribution C2 for an HDL cholesterol level, a factor-specific contribution C3 for a blood pressure value, a factor-specific contribution C4 for a smoking status, and a factor-specific contribution C5 for diabetes. Formulas (2) to (6) below are an example of a calculation formula used in the calculation of the factor-specific contributions C1 to C5. Since the factor-specific evaluation values D1 and D3 to D5 are a positive value, the factor-specific contributions C1 and C3 to C5 are a positive value. Since the factor-specific evaluation value D2 is a negative value, the factor-specific contribution C2 is a negative value.

[Equation 2]

$$C1 = \frac{D1}{D1 + D3 + D4 + D5} \quad (2)$$

$$C2 = \frac{D2}{D1 + D3 + D4 + D5} \quad (3)$$

$$C3 = \frac{D3}{D1 + D3 + D4 + D5} \quad (4)$$

$$C4 = \frac{D4}{D1 + D3 + D4 + D5} \quad (5)$$

$$C5 = \frac{D5}{D1 + D3 + D4 + D5} \quad (6)$$

In the present embodiment, a total value of the factor-specific evaluation values D1 and D3 to D5 for negative factors is used as an additional value acquired by totaling factor-specific evaluation values for improvable factors. For example, the factor-specific contribution C1 is a contribution degree of the total cholesterol level to the ASCVD occurrence risk R within 10 years. The factor-specific contribution C1 is calculated as a proportion of the factor-specific evaluation value D1 to the total value of the factor-specific evaluation values D1 and D3 to D5 for the negative factors. The factor-specific contribution C2 to C5 are also calculated similarly to the factor-specific contribution C1.

Next, the processor 80a generates output data by using the calculation results in S113 and S114 (S115). The output data is, for example, image data displayed on the display unit 35 of the portable terminal 30 or the display unit 55 of the fixed terminal 50. The generated output data is stored in the output data storage unit 89 of the memory 80b, for example.

Next, the processor 80a outputs the output data generated in S115 to the outside (S116). The processor 80a outputs the output data to the control unit 31 of the portable terminal 30, for example. The output data being output is displayed on, for example, the display unit 35 by the control unit 31.

2.4.3 Display Example

FIG. 13 is a diagram illustrating an example of a display screen used for inputting biological information and behavior information. The display screen in FIG. 13 is displayed on the display unit 35 of the portable terminal 30, for example. The display screen in FIG. 13 may be displayed on the display unit 55 of the fixed terminal 50, for example.

In the display screen in FIG. 13, an input information display portion 91 and a risk display portion 92 are provided. In the input information display portion 91, input information relating to the evaluation subject is displayed. The input information is input to the operation unit 34, for example. In the risk display portion 92, a calculation result of the ASCVD occurrence risk R within 10 years is displayed.

In the input information display portion 91, one of "Men" and "Women" is displayed for gender (Gender). "Men" indicates that the evaluation subject is male, and "Women" indicates that the evaluation subject is female.

Further, in the input information display portion 91, one of "White" and "AA" is displayed for race (Race). "White" indicates that the evaluation subject is White, and "AA" indicates that the evaluation subject is African American.

Further, in the input information display portion 91, age of the evaluation subject is displayed for age (Age). Further, in the input information display portion 91, a total cholesterol level (mg/dL) of the evaluation subject is displayed for a total cholesterol level (Total Cholesterol). Further, in the input information display portion 91, an HDL cholesterol level (mg/dL) of the evaluation subject is displayed for an HDL cholesterol level (High Density Lipoprotein-Cholesterol).

Further, in the input information display portion 91, one of "Treated" or "Untreated" is displayed for presence or absence of hypertension treatment (Hypertension Treatment). "Treated" indicates that treatment is being received for hypertension treatment using an antihypertensive drug. "Untreated" indicates that treatment is not yet received for hypertension treatment using an antihypertensive drug.

Further, in the input information display portion 91, a blood pressure value (mmHg) of systolic blood pressure of the evaluation subject is displayed for a blood pressure value of systolic blood pressure (Systolic BP).

Further, in the input information display portion 91, one of "Yes" and "No" is displayed for a smoking status (Current Smoker). "Yes" indicates that the evaluation subject is a smoker. "No" indicates that the evaluation subject is not a smoker.

Further, in the input information display portion 91, one of "Yes" and "No" is displayed for presence or absence of diabetes (Diabetes). "Yes" indicates that the evaluation subject is diabetic. "No" indicates that the evaluation subject is not diabetic.

FIG. 13 illustrates an example when the evaluation subject is male, is White, is 50 years old, has a total cholesterol level of 150 mg/dL, has an HDC cholesterol level of 50 mg/dL, has an antihypertensive drug being already used, has a blood pressure value of systolic blood pressure of 150 mmHg, is a smoker, and is a diabetic patient.

FIG. 14 is a diagram illustrating an example of a display screen indicating a calculation result of the factor-specific contributions C1 to C5 when the input information illustrated in FIG. 13 is acquired. The display screen in FIG. 14 is displayed on the display unit 35 of the portable terminal 30, for example. The display screen in FIG. 14 may be displayed on the display unit 55 of the fixed terminal 50.

In the display screen in FIG. 14, a contribution display portion 93 is provided. In the contribution display portion 93, the factor-specific contribution C1 for a total cholesterol level (Total Cholesterol), the factor-specific contribution C2 for an HDL cholesterol level (HDL-C), the factor-specific contribution C3 for a blood pressure value (BP), the factor-specific contribution C4 for a smoking status (Smoking), and the factor-specific contribution C5 for presence or absence of diabetes (Diabetes) are displayed.

FIG. 15 is a diagram illustrating an example of a display screen in which output data generated by the contribution calculation processing described above is displayed when the input information illustrated in FIG. 13 is acquired. The display screen in FIG. 15 is displayed on the display unit 35 of the portable terminal 30, for example. The display screen in FIG. 15 may be displayed on the display unit 55 of the fixed terminal 50, for example.

The display screen in FIG. 15 includes a graph 94 and a graph 95. The graph 94 is a stacked bar graph with each of negative factors as a component. The vertical axis of the graph 94 is a factor-specific contribution and a unit is %. The factor-specific contribution for the negative factor includes the factor-specific contribution C1 for a total cholesterol level (Total Cholesterol), the factor-specific contribution C3 for a blood pressure value (BP), the factor-specific contribution C4 for a smoking status (Smoking), and the factor-specific contribution C5 for presence or absence of diabetes (Diabetes).

The graph 95 is a stacked bar graph with a positive factor as a component. The vertical axis of the graph 95 is a factor-specific contribution and a unit is %. The factor-specific contribution for the positive factor includes the factor-specific contribution C2 for an HDL cholesterol level (HDL-C). Note that the graphs 94 and 95 may be a circular graph and the like.

Note that, in the graphs 94 and 95, as a component of the graph, an integrated value of each of the factor-specific contributions C1 to C5 and the ASCVD occurrence risk R within 10 years may be used. In this case, the ASCVD occurrence risk R within 10 years is used for the vertical axis of the graphs 94 and 95.

Further, in the display screen, a factor having a greatest factor-specific contribution may be selected from among the negative factors, and only a name and the factor-specific contribution for the selected factor may be displayed.

2.5 Actions and Effects

In the present embodiment, the processor 80*a* of the risk evaluation circuit 80 generates output data, based on a calculated factor-specific contribution. According to the present embodiment, a cause that greatly pushes up the ASCVD occurrence risk within 10 years can be easily recognized by comparing contributions to the ASCVD occurrence risk within 10 years by factor. In this way, it is clear which measurement result pushes up the risk, and it is easy for a user to determine how to reduce the risk.

Further, according to the present embodiment, for example, even when an evaluation of input information about all factors falls within a normal range, the user can recognize a cause that greatly contributes to an increase in risk by comparing contributions to an event occurrence rate by factor.

Further, in the present embodiment, an item that can be improved by an evaluation subject among acquired input information is extracted as an improvable factor. Then, a factor-specific contribution to the ASCVD occurrence risk within 10 years is presented for the extracted improvable item. Thus, according to the present embodiment, the user can easily recognize a cause that is improvable and greatly contributes to a reduction in risk, and can easily determine how to reduce the risk.

3. Common Configuration in Embodiment and the Like

A risk management device (1:40) includes an acquisition unit (2:42) configured to acquire biological information relating to a biological parameter of an evaluation subject and behavior information relating to a behavior parameter of the evaluation subject, a risk calculation unit (3:43) configured to calculate an event occurrence rate, based on the biological information being acquired and the behavior information being acquired, a selection unit (4:44) configured to select a biological parameter and a behavior parameter that serve as an improvable factor from the biological information and the behavior information, a contribution calculation unit (5:45) configured to calculate a contribution to the event occurrence rate for each of the biological parameter and the behavior parameter selected as the improvable factor, and a generation unit (6:46) configured to generate output data indicating a calculation result in the contribution calculation unit (5:45).

Note that the present invention is not limited to the embodiment, and various modifications can be made in an implementation stage without departing from the gist. Further, embodiments may be carried out as appropriate in a combination, and combined effects can be obtained in such case. Further, the various inventions are included in the embodiment, and the various inventions may be extracted in accordance with combinations selected from the plurality of disclosed constituent elements. For example, in a case where the problem can be solved and the effects can be obtained even when some constituent elements are removed from the entire constituent elements given in the embodiment, the configuration obtained by removing the constituent elements may be extracted as an invention.

Supplementary Notes

A part or the entirety of the embodiment can be described, as described in the following supplementary notes in addition to the scope of the claims, but the present invention is not limited thereto.

Supplementary Note 1

A risk management device, including
a hardware processor and a memory, wherein
the hardware processor is configured to
acquire biological information relating to a biological parameter of an evaluation subject and behavior information relating to a behavior parameter of the evaluation subject, and store the biological information and the behavior information in the memory,
calculate an event occurrence rate, based on the biological information and the behavior information stored in the memory,
select a biological parameter and a behavior parameter that serve as an improvable factor from the biological information and the behavior information stored in the memory,
calculate a contribution to the event occurrence rate for each of the biological parameter and the behavior parameter selected as the improvable factor, based on information relating to the biological parameter and the behavior parameter selected as the improvable factor among the biological information and the behavior information stored in the memory, and store the contribution in the memory, and
generate output data, based on the contribution stored in the memory.

Supplementary Note 2

A risk management method performed by a device that includes a hardware processor and a memory, the risk management method including
a step of, by the hardware processor, acquiring biological information relating to a biological parameter of an evaluation subject and behavior information relating to a behavior parameter of the evaluation subject, and storing the biological information and the behavior information in the memory,
a step of, by the hardware processor, calculating an event occurrence rate, based on the biological information and the behavior information stored in the memory,
a step of, by the hardware processor, selecting a biological parameter and a behavior parameter that serve as an improvable factor from the biological information and the behavior information stored in the memory,
a step of, by the hardware processor, calculating a contribution to the event occurrence rate for each of the biological parameter and the behavior parameter selected as the improvable factor, based on information relating to the biological parameter and the behavior parameter selected as the improvable factor among the biological information and the behavior information stored in the memory, and storing the contribution in the memory, and a step of, by the hardware processor, generating output data, based on the contribution stored in the memory.

REFERENCE SIGNS LIST

1 Risk management device
2 Acquisition unit
3 Risk calculation unit
4 Selection unit
5 Contribution calculation unit
6 Generation unit
10 Blood pressure measurement device
11 Control unit
12 Storage unit
13 Communication unit
14 Operation unit
15 Display unit
16 Blood pressure sensor
17 Acceleration sensor
18 Temperature/humidity sensor
30 Portable terminal
31 Control unit
32 Storage unit
33 Communication unit
34 Operation unit
35 Display unit
36 GPS receiver
50 Fixed terminal
51 Control unit
52 Storage unit
53 Communication unit
54 Operation unit
55 Display unit
70 Server
71 Control unit
72 Storage unit
73 Communication unit
80 Risk evaluation circuit
80a Processor
80b Memory
82 Acquisition unit
83 Risk calculation unit
84 Selection unit
85 Contribution calculation unit
86 Generation unit
87 Input information storage unit
88 Evaluation information storage unit
89 Output data storage unit
91 Input information display portion
92 Risk display portion
93 Contribution display portion
94, 95 Graph
A Evaluation calculation value
BS Survival rate
C1 to C5 Factor-specific contribution
D1 to D5 Factor-specific evaluation value
K1 to K13 Coefficient
M Reference value
N1 to N6 Variable
P1 to P13 Integrated value

The invention claimed is:

1. A risk management device, comprising:
a processor configured to:
acquire biological information relating to a biological parameter of an evaluation subject and behavior information relating to a behavior parameter of the evaluation subject;
calculate an event occurrence rate, based on the biological information being acquired and the behavior information being acquired;
select the biological parameter and the behavior parameter that serve as an improvable factor from the biological information and the behavior information;
calculate a contribution to the event occurrence rate for each of the biological parameter and the behavior parameter selected as the improvable factor; and
generate output data indicating a calculation result in the contribution calculation unit, wherein
the processor calculates an evaluation value for the event occurrence rate for each of the biological parameter and the behavior parameter selected as the improvable factor, calculates an additional value acquired by totaling the calculated evaluation values, and calculates, as the contribution, a proportion of each of the evaluation value of the biological parameter and the evaluation value of the behavior parameter to the calculated additional value,
the improvable factor includes a negative factor that contributes to an increase in the event occurrence rate and a positive factor that contributes to a reduction in the event occurrence rate, and
the processor calculates, as the additional value, a total value of the evaluation value calculated for each of the biological parameter and the behavior parameter selected as the negative factor of the improvable factor.

2. The risk management device according to claim 1, wherein
the processor calculates an occurrence risk of arteriosclerotic cardiovascular disease as the event occurrence rate.

3. The risk management device according to claim 1, wherein
the processor acquires, as the biological information, at least one of race, gender, age, a blood pressure value, a cholesterol level, presence or absence of diabetes, and genetic information.

4. The risk management device according to claim 1, wherein
the processor acquires at least one of a smoking status and sleep time as the behavior information.

5. The risk management device according to claim 1, wherein
the processor selects, as the improvable factor, at least one of a blood pressure value, a cholesterol level, presence or absence of diabetes, presence or absence of smoking, and sleep time.

6. The risk management device according to claim 1, wherein
the processor generates, as the output data, image data configured to compare the contributions of the biological parameter and the behavior parameter selected as the improvable factor with each other.

7. A risk management method executed by a device configured to manage an event occurrence rate relating to an evaluation subject, the risk management method comprising:
acquiring biological information relating to a biological parameter of the evaluation subject and behavior information relating to a behavior parameter of the evaluation subject;
calculating an event occurrence rate, based on the biological information being acquired and the behavior information being acquired;

selecting the biological parameter and the behavior parameter that serve as an improvable factor from a plurality of biological parameters and the behavior parameters included in the biological information and the behavior information;
calculating a contribution to the event occurrence rate for each of the biological parameter and the behavior parameter selected as the improvable factor; and
generating output data indicating a calculation result of the contribution, wherein
calculating the contribution calculates an evaluation value for the event occurrence rate for each of the biological parameter and the behavior parameter selected as the improvable factor, calculates an additional value acquired by totaling the calculated evaluation values and calculates, as the contribution, a proportion of each of the evaluation value of the biological parameter and the evaluation value of the behavior parameter to the calculated additional value,
the improvable factor includes a negative factor that contributes to an increase in the event occurrence rate and a positive factor that contributes to a reduction in the event occurrence rate, and
calculating the contribution calculates, as the additional value, a total value of the evaluation value calculated for each of the biological parameter and the behavior parameter selected as the negative factor of the improvable factor.

* * * * *